United States Patent [19]

Akutsu et al.

[11] Patent Number: 4,865,448
[45] Date of Patent: Sep. 12, 1989

[54] METHOD AND APARATUS FOR OBSERVING THE INTERNAL SURFACE OF A SMALL HOLE

[75] Inventors: Kenzo Akutsu, Takatsuki; Takashi Shiraishi, Nagaokakyo, both of Japan

[73] Assignees: Sanko Giken Kogyo Co., Ltd., Japan; OEM Systems Co., Ltd., Japan

[21] Appl. No.: 162,685

[22] Filed: Mar. 1, 1988

[51] Int. Cl.$^4$ ............................................. G01N 21/88
[52] U.S. Cl. ..................................... 356/241; 250/563
[58] Field of Search ................. 356/241; 250/562, 563

[56] References Cited

U.S. PATENT DOCUMENTS 4,268,169 5/1981 Stenning ............................ 356/241
4,560,273 12/1985 Ando et al. ..................... 356/241 X

OTHER PUBLICATIONS

Johnson et al., "Optical System for Viewing Dielectric Smear in Printed Circuit Board Hole and Deleting the Smear", *IBM Tech. Disclos. Bull.*, vol. 25, No. 9, pp. 4513-4514.

*Primary Examiner*—Davis L. Willis
*Assistant Examiner*—Matthew W. Koren
*Attorney, Agent, or Firm*—Barnes, Kisselle, Raisch, Choate, Whittemore & Hulbert

[57] ABSTRACT

A reflecting surface is formed at the utmost end of a smaller diameter wire rod, and the utmost end portion thereof is inserted into a small hole to image the internal surface thereof. A laser beam is incident on the reflecting surface and impinged on the internal surface of the small hole while rotating the smaller diameter wire rod inserted into the small hole around the axis of the smaller diameter wire rod and relatively to the small hole. The laser beam reflected from the internal surface of the small hole and subsequently the reflecting surface is reflected by a half-silvered mirror provided in the way of an optical path of the laser beam and guided to an image processor. The condition of the small hole is observed by the image processor. Thereby the condition of the internal surface of the small hole is observed without breaking down an inspected object.

2 Claims, 8 Drawing Sheets

FIG. 2
FIG. 3
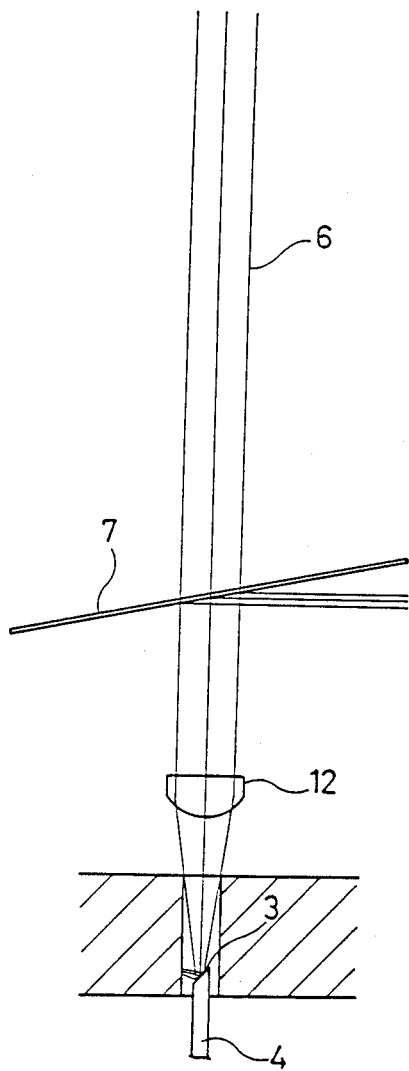
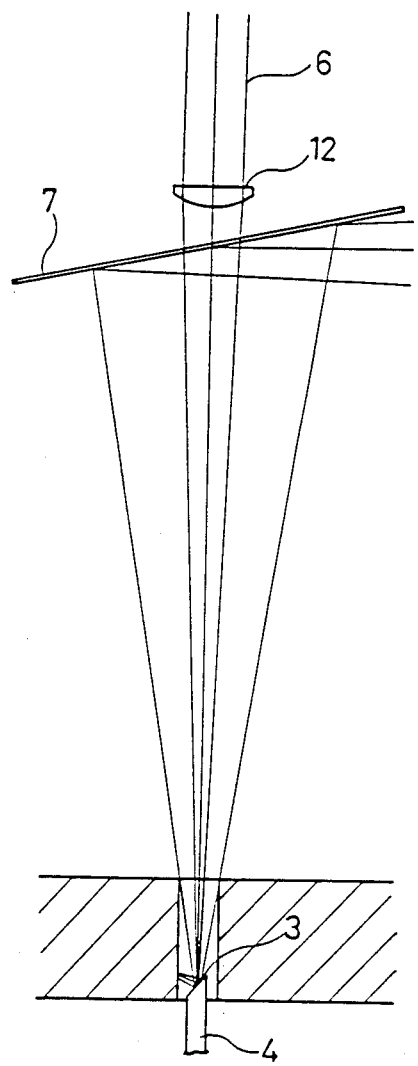

METHOD AND APARATUS FOR OBSERVING THE INTERNAL SURFACE OF A SMALL HOLE

FIELD OF THE INVENTION

The present invention relates to a method and an apparatus for observing the internal surface of a small hole, such as a plated through-hole in a multilayer printed wiring board.

BACKGROUND OF THE INVENTION

Generally, a multilayer printed wiring board is composed of a plurality of copper-plated plates laminated and pressed, and the layers are electrically connected therebetween to form a multilayer printed wiring board. Such interlayer connection is formed in such a manner that a small hole is formed at a predetermined portion of the multilayer printed board by use of a drill so that the small hole is plated (through-hole-plated) at the internal surface thereof. Each layer at the multilayer printed board comprises copper foil and an epoxy resin impregnated base material setting layer. When the small hole is formed by use of an old drill, the epoxy resin of the epoxy resin impregnated base metal setting layer melts by the frictional heat and covers the copper foil part appearing at the internal surface of the hole, the covered portion being called the smear. Therefore, even when a plated layer is formed at the internal surface of the small hole, the smeared part causes a poor electrical connection between the plated layer and the copper foil, resulting in poor conduction. Also, in a case where the old drill is used to form a small hole in the multilayer printed board, as above-mentioned, the internal surface of the small hole becomes rough so that air foam becomes attached to the rough surface at the time of the plating to cause disconnecting of a portion at the plated layer, resulting in poor conduction.

In a case where the small hole is formed in the multilayer printed board, when the smear is produced at the internal surface of the small hole or the internal surface becomes rough, the plated layer of through-hole plating is poor in conduction, whereby prior to the through-hole plating, the internal surface condition of the small hole has been observed. When a hole diameter is larger or the board is small in thickness, the internal surface can be observed obliquely by use of a microscope. However, when the hole diameter is very small as 0.3 to 4 mm, it is impossible to observe the internal surface reflected by a small mirror inserted into the hole or to observe obliquely the entire surface. Hence, an object to be inspected is sampled for inspection and subjected to a breakdown test to thereby observe the internal surface of the hole. In detail, the multilayer printed board to be inspected is sampled and cut by intersecting the hole so that the internal surface is visually inspected or observed by an electron micrograph. Such observation, however, takes much time and breaks down the object to be inspected, thereby being unreasonable.

SUMMARY OF THE INVENTION

An object of the present invention is to provide a method and an apparatus which are capable of observing the internal surface of a small hole with ease and without breaking down a object to be inspected.

In order to attain the above object, the method for observing the internal surface of the small hole of present invention is characterized in that; a smaller diameter wire rod smaller in diameter than the hole and having at the utmost end a reflecting surface is inserted at the utmost end portion into the hole coaxially therewith; a laser beam is impinged onto the utmost end surface through a half-silvered mirror while rotating the smaller diameter wire ord relatively to the internal surface of the hole, so that the laser beam is reflected from the reflecting surface and impinged onto the internal surface of the hole; the laser beam reflected from the internal surface is reflected by the reflecting surface, reaches the half-silvered mirror, and is reflected therefrom; and the reflected laser beam reflected by the half-silvered mirror is guided to image processing means;.

The apparatus for observing the internal surface of the small hole of present invention comprises a measuring table for loading thereon an object to be inspected, a smaller diameter wire rod having at the utmost end a reflective surface slanted to the axis of the hole, measuring table moving means for moving the measuring table so as to position the utmost end portion of the smaller diameter wire rod coaxially in the hole of the object to be inspected, means for allowing the smaller diameter wire rod to rotate around the axis thereof and relative to the hole, means for moving the reflecting surface of the utmost end of the smaller diameter wire rod from an opening at one end to that at the other end of the hole relative thereto, a laser beam source from which the laser beam is impinged onto the reflecting surface of the smaller diameter wire rod and then reflected from the reflecting surface so as to be impinged onto the internal surface of the hole, a half-silvered mirror which is disposed to slantwise intersect the laser beam impinged from the laser beam source to the reflecting surface of the smaller diameter wire rod and reflects the laser beam reflected from the reflecting surface after reflected by the internal surface of the hole, and recording and displaying means for receiving the laser beam reflected by the half-silvered mirror and image-processing the laser beam so that an image of the internal surface of the hole is recorded and displayed.

According to the observing method and apparatus of the invention of the above-mentioned construction, the internal surface of the small hole can be observed with ease and without breaking down the object to be inspected, thereby being extremely effective in observing the condition of the internal surface of the small hole in the multilayer printed board or plating condition of the internal surface of the plated through-hole of the multilayer printed wiring board.

BRIEF DESCRIPTION OF THE DRAWINGS

FIG. 2 is a schematic diagram showing an example of a construction in which a lens is disposed in an optical path of the laser beam in the optical system in FIG. 1, FIG. 3 is a schematic diagram showing another example of a construction in which a lens is disposed in an optical path of the laser beam in the optical system in FIG. 1.

DETAILED DESCRIPTION OF THE PREFERRED EMBODIMENT OF THE INVENTION

Figure 14:
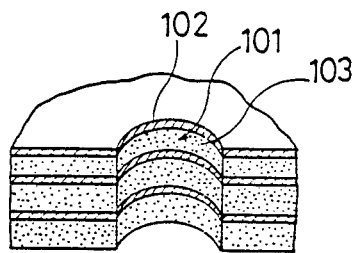
FIG. 14 is a diagram showing a multilayer printed board cut at the small hole.

Referring to FIG. 14, a multilayer printed board as an object to be inspected is shown in section. The multilayer printed board comprises copper foil 102, epoxy resin impregnated base material setting layers 103, and a small hole 101 formed in the board by use of a drill.

Figure 1:
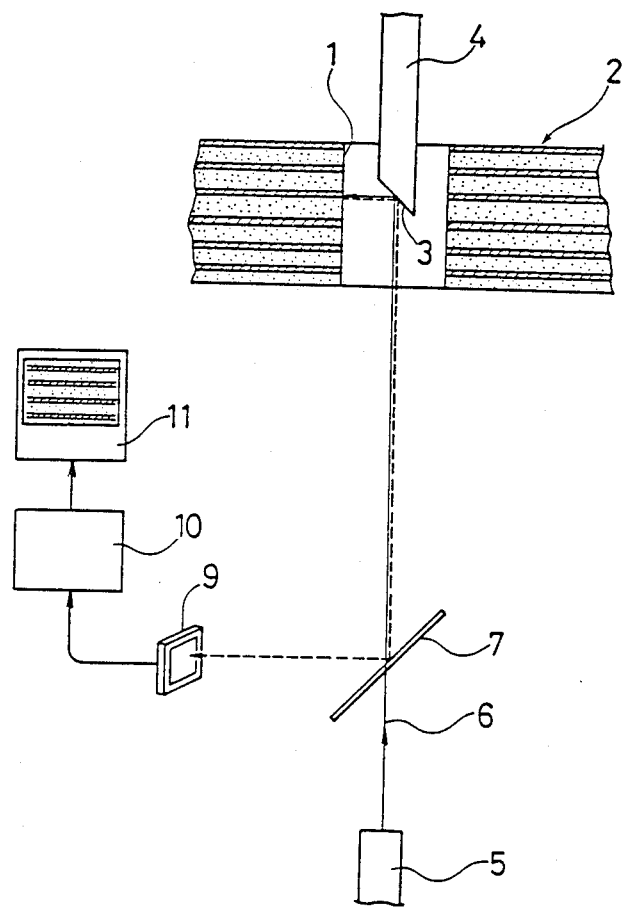
FIG. 1 is a schematic diagram showing the fundamental principle of the present invention.

The principle of the present invention is shown in FIG. 1, in which reference numeral 2 designates the multilayer printed board in which a small hole 1 is formed by the drill. A smaller diameter wire rod 4 providing at the utmost end a reflecting surface (mirror) 3 is inserted at the utmost end portion within the hole 1, co-axially therewith. The wire rod 4 is formed of a metallic thin wire, a glass thin wire, or a plastic thin wire, the reflecting surface 3 being formed by grinding or vapor deposition of metal. A laser beam 6 is impinged from a laser beam source 5 directly (without striking the internal surface of the hole 1) onto the reflecting surface 3 via a half-silvered mirror 7 as shown by the solid line in FIG. 1. The impinged laser beam 6 is reflected by the reflecting surface 3, reaches the internal surface of the hole 1, is reflected therefrom to return to the reflecting surface 3 as shown in the broken line, and is reflected by the half-silvered mirror 7 to reach a photosensor 9. The projected image of the internal surface of the hole 1 is displayed on a display 11 through an image processing circuit 10. The smaller diameter wire rod 4 is rotated around the axis thereof, thereby enabling the entire internal surface of the hole 1 to be imaged. The reflecting surface 3 of the utmost end of the smaller diameter wire rod 4 is moved from an opening at one end to that at the other end of the hole 1 while being rotated, thereby enabling observation of the entire internal surface of the hole 1 from the opening at the one end to that at the other end. In this case, the laser beam 6 impinged from the laser beam source 5 is focused on the internal surface of the hole 1 so that an extremely clear image is obtainable. For this purpose, it is preferable to dispose a lens in the optical path of the laser beam 6. Such condition is shown in FIGS. 2 and 3. In FIG. 2, a convex lens 12 is disposed ahead of the half-silvered mirror 7 in the optical path, and in FIG. 3, behind the same.

The above arrangement can readily observe the internal surface of the hole 1 provided in the object to be inspected, such as the multilayer printed board 2, without breaking down the object.

Figure 4:
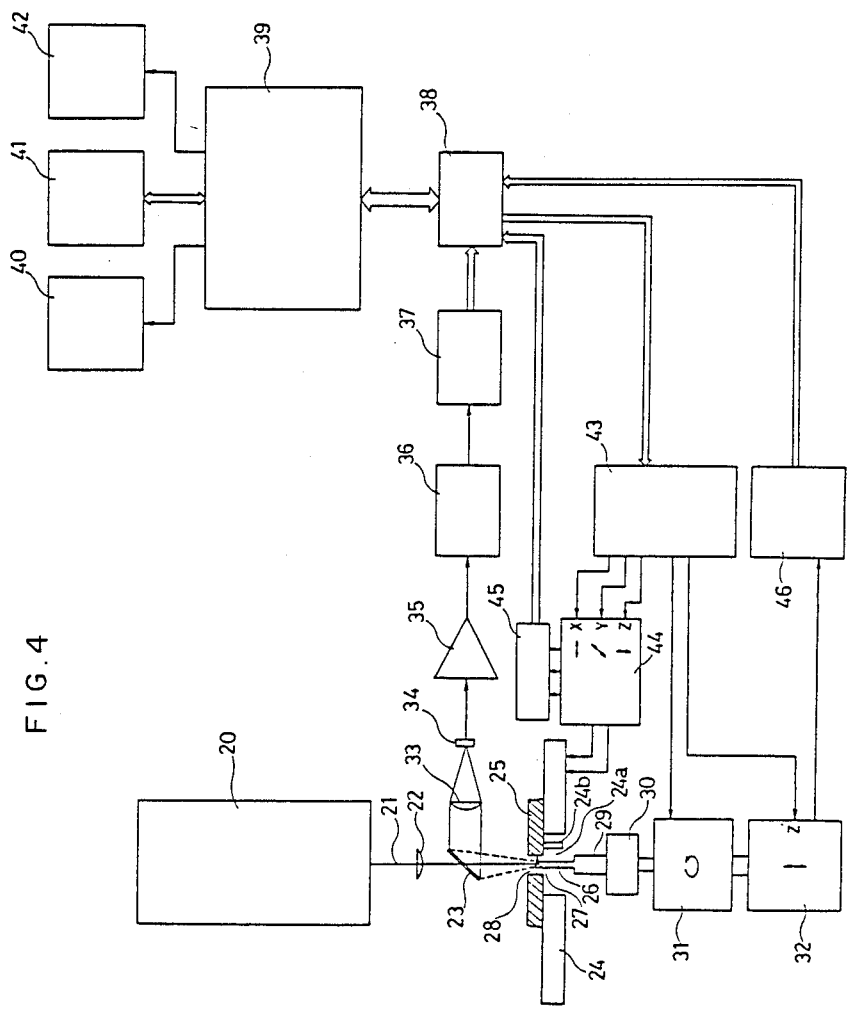
FIG. 4 is a block diagram of an embodiment of an observing apparatus for the internal surface of a small hole in accordance with present invention.

In FIG. 4, an embodiment of the apparatus of the invention is shown, in which reference numeral 20 designates a He—Ne laser beam source, from which a laser beam 21 is impringed as shown by the solid line. Numeral 22 designates a convex lens disposed in the optical path. Numeral 23 designates a half-silvered mirror disposed in the optical path. Numeral 24 designates a measuring table consisting of an X-Y table. Numeral 25 designates a multilayer printed board as an object to be inspected and placed on the measuring table 24. Numeral 26 designates a smaller diameter wire rod provided at the utmost end with a reflecting surface 27 slantiwise to the axial direction of the optical path. The utmost end of the smaller diameter wire rod 26 is inserted co-axially into a small hole 28 in the multilayer printed board 25.

The smaller diameter wire rod 26 is connected at the base thereof to a rotary mechanism 30, which is driven by a wire rod rotating motor 31 and a wire rod translating mechanism 32 for moving the wire rod vertically. In the measuring table 24 is formed a bore 24a relatively larger in diameter, and a fixed reflecting surface body 24b is fixedly positioned at an inner portion of the bore 24a. The multilayer printed board 25 is placed on the measuring table 24 putting the hole 28 in alignment with the bore 24a of the table 24. Reference numeral 33 designates a light convergent lens for converging the reflected light from the half-silvered mirror 23 and transmitting it to a photosensor 34, which detects variation in the amount of light received. Numeral 35 designates an amplifier for amplifying a signal of the photosensor 34, 36 designates an analog signal processing circuit, 37 designates an A/D converter, 38 designates an interface, 39 designates a computer to which a printer 40, a floppy disc 41 and an image display means 42 consisting of CRT are connected, 43 designates a motor driver, 44 designates a driver mechanism for the measuring table 24, 45 designates a first position detecting circuit connected to the drive mechanism 44 for the measuring table 24, and 46 designates a second position detecting circuit connected to the wire rod translating mechanism 32.

Figure 5:
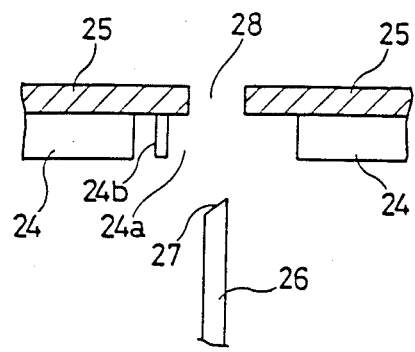
FIGS. 5 through 13 are schematic views which explain the operation of the apparatus shown in FIG. 4.
Figure 6:
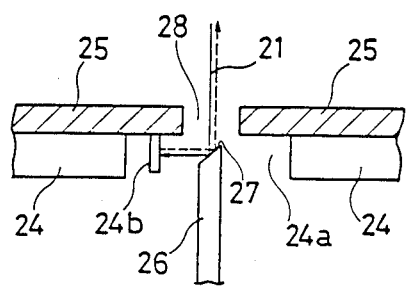

The apparatus of the above-mentioned construction is used to observe the internal surface of the hole 28 at the multilayer printed board 25 as follows. The apparatus for observing the internal surface of the hole 28 is switched on and the laser beam 21 is impringed from the laser beam source 20. Next, as shown in FIG. 5, the measuring table is manually operated, and the axis of smaller diameter wire rod 26 is roughly aligned with the center of the hole 28 of the printed board 25 to allow the laser beam 21 to pass through the hole 28. In such condition, the utmost end of the smaller diameter wire rod 26 is positioned below the measuring table 24 as shown in FIG. 5. Then in this condition, the measuring table 24 is manually lowered and the reflecting surface 27 at the smaller diameter wire rod 26, as shown in FIG. 6, is positioned at the same level with the fixed reflecting surface member 24b, thereby allowing th laser beam 21 to impinge on the surface member 24b. In this condition, the laser beam 21 reaches the reflecting surface 27 and is reflected therefrom to illuminate the fixed reflecting surface member 24b as shown by the solid line in FIG. 6. The laser beam 21 is reflected by the reflecting surface member 24b so as to reach the half-silvered mirror 23 (refere to FIG. 4) through the reflecting surface 27 of the smaller diameter wire rod 26 and reach the photosensor 34 through the convex lens 33 for converging the laser beam. In this condition, the laser beam reflected from the reflecting surface 27 at the upper end of smaller diameter wire rod 26 is entirely incident on the photosensor 34, thereby maximizing the amount of light received by the photosensor 34.

Figure 7:
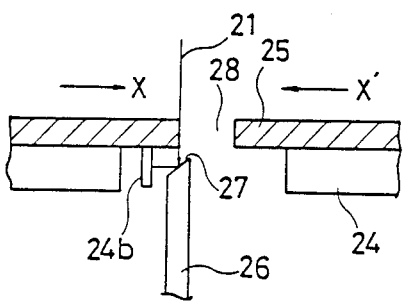

Then, the computer 39 puts out a signal to move the measuring table 24 in the direction of the arrow X as shown in FIG. 7. As a result, the reflected light of the laser beam 21 is shaded by the edge at one side of the hole 28, thereby reducing the quantity of the laser beam 21 impinged onto the photosensor 34. A signal for the change in the quantity of beam is transferred to the computer 39, which puts out a signal to stop movement of the measuring table 24 in the direction of the arrow X. Next, the computer 39 puts out the signal to move the measuring table 24 in the reverse direction to the above (the direction of the arrow X' in FIG. 7). In this condition, since nothing shades the reflected light of the laser beam 21, the quantity of light incident on the photosensor 34 becomes maximum. When the measuring table 24 is further moved in the reverse direction (the direction of the arrow X' in FIG. 7), the other side edge of the hole 28 of the multilayer printed board 25 shades the reflected laser beam 21, thereby reducing the quantity of beam incident on the photosensor 34. At this time, similarly to the above, the computer 39 puts out a signal due to the change in the quantity of beam to thereby stop the movement of the measuring table 24.

Figure 8:
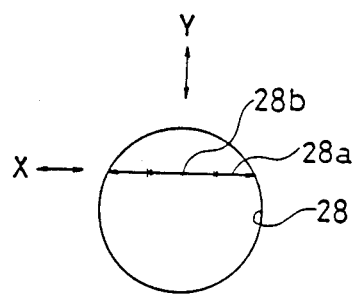

In the above description, the laser beam 21 is reflected by means of the reflecting surface member 24b and detected by the photosensor 34, but the reflecting surface member 24b may alternatively be replaced by a photosensor to thereby enable the change in quantity of beam to be directly detected. An amount of movement (movement in the direction of the arrow X) of the measuring table 24 from the edge at one side to that at the other side of the hole 28 is detected by a first position detection circuit (composed of, for example, a rotary encoder) 45 connected to the drive mechanism 44, the detected value being transferred to the computer 39. As a result, the computer 39 makes an operation for the value to obtain a half value of the movement of measuring table 24 in the direction of the arrow X. The half value corresponds to one point on the center line of the hole 28 in the direction of the arrow Y as shown in FIG. 8. In FIG. 8, reference numeral 28a designates a movement path of the laser beam 21 in the direction X. Since the laser beam 21 is manually positioned, its movement path 28a does not pass the center of hole 28, but is somewhat offset therefrom. Numeral 28b designates a point of a half value of a moving amount in the direction X, the point being positioned on the center line in the direction Y, whereby the center line in the direction Y is consequently obtained.

Figure 9:
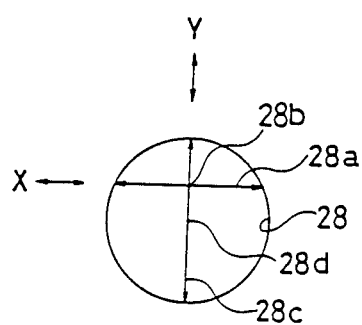
Figure 10:
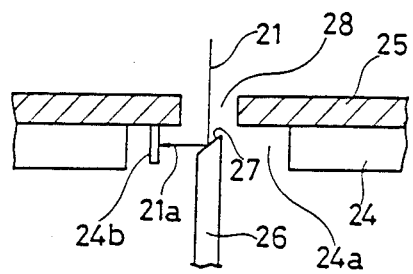

Then, the computer 39 put outs a signal to move the measuring table 24, thereby allowing the laser beam 21 to pass through the point 28b which is positioned on the center line in the direction Y. Then, the measuring table 24 is moved in the direction Y from the above condition to obtain a half value of movement of the table 24 in the direction Y by a method similar to that for obtaining the point 28b. This half value coincides with a point on the center line of the hole 28 in the direction X, which is shown in FIG. 9. In FIG. 9, reference numeral 28c designates a movement path of the laser beam 21 in the direction Y and 28d designates the point of half value of movement of the table 24 in the direction Y. The point 28d finally shows the center of the hole 28, and the length of movement path 28c in the direction Y shows a diameter of the hole 28. Thus, the center and diameter of the hole 28 are obtainable. And the computer 39 drives the measuring table driving mechanism 44 to align the axis of smaller diameter wire rod 26 with the center of hole 28, thereby moving the measuring table 24 in the directions X and Y. As a result, as shown in FIG. 10, the axis of the smaller diameter wire rod 26 is automatically aligned with the center of hole 28.

Figure 11:
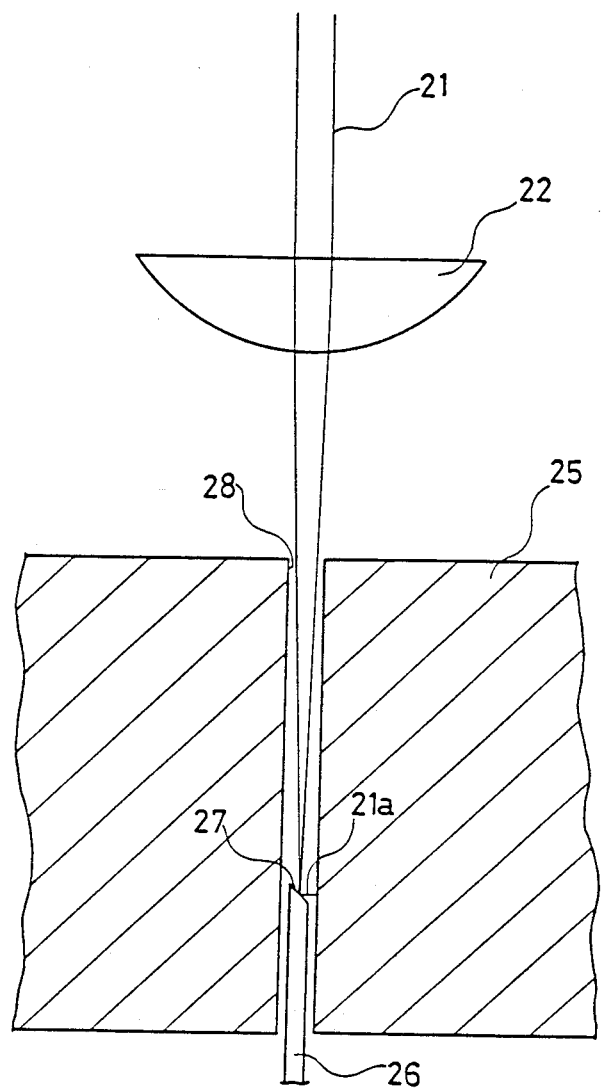
Figure 12:
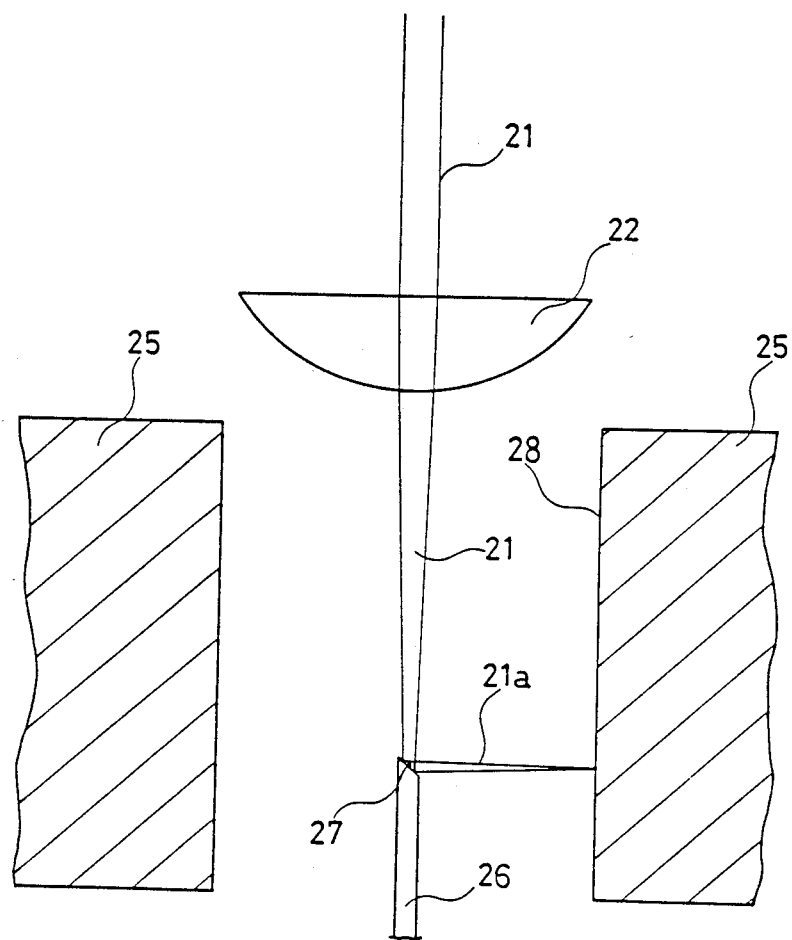

Then, the computer 39, in such condition, puts out a signal to drive the wire rod translating mechanism 32 to thereby vertically move (in the direction of the arrow Z' in FIG. 4) the small diameter wire rod 26, and thereby the reflecting surface 27 thereof is moved toward or away from the convex lens 22. Hence, the laser beam 21 reflected by the reflecting surface of the wire rod 26 is focused on the internal surface of the hole 28. For example, when the hole 28 is smaller in diameter, the distance b between the reflecting surface 27 of the smaller diameter wire rod 26 and the convex lens 22 is increased as shown in FIG. 11, so that the reflected laser beam 21a of the laser beam 21 is adapted to be focused on the internal surface of the hole 28. On the other hand, when the hole 28 is larger in diameter, that same distance decreases as shown in FIG. 12 so that the reflected laser beam 21a is adapted to be focused on the internal surface of the hole 28. The position of small diameter wire rod 26 is obtained by computing an input value of a focal distance of convex lens 22 previously given to the computer 39 and the diameter of the hole 28 obtained as above-mentioned, the smaller diameter wire rod 26 being moved as above-mentioned on the basis of the computed value.

The amount of movement of smaller diameter wire rod 26 appears larger when viewed in FIGS. 11 and 12, which exaggerates the movement of wire rod 26 for easy understanding. In fact, the hole 28 is quite small in diameter and its movement is small. Therefore, even when the wire rod 26 moves, for example, to a maximum, the reflecting surface 27 thereof remains in the bore 24a of the measuring table 24 as shown in FIG. 10.

After the smaller diameter wire rod 26 is vertically moved to allow the reflected beam 21a of laser beam 21 to be thus forcused or the internal surface of the hole 28, the computer 39 puts out a signal to drive the measuring table driving mechanism 44 and lower (move in the direction of the arrow Z) the measuring table 24, thereby positioning the reflecting surface 27 of wire rod 26 at the lower end of the hole 28. The positioning is performed on the basis of a difference between the quantity of reflected laser beam 21 reflected by the reflecting surface of the fixed reflecting surface member 24b and that reflected by the internal surface of the hole 28 of the printed board 25 (where the quantity of reflected beam from the internal surface of the hole 28 is smaller). That is, when the measuring table 24 lowers so that the reflecting surface 27 shifts from the reflecting surface member 24b and corresponds to the internal surface of hole 28, the quantity of reflected laser beam largely decreases, whereby the computer 39 puts out the signal to stop lowering of the measuring table 24. As a result, the reflecting surface 27 is automatically positioned at the lower end of the hole 28.

Figure 13:
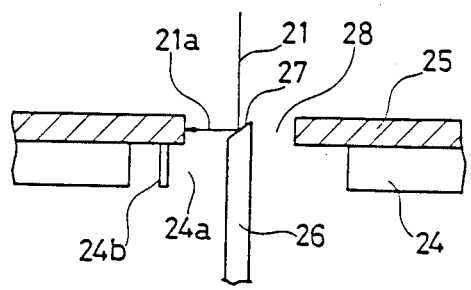

Then, in the above condition, the computer 39 puts out a signal, the smaller diameter wire rod rotating motor 31 is rotatably driven, the smaller diameter wire rod 26 is rotated around the axis thereof, and simultaneously the measuring table driving mechanism 44 is driven to gradually lower (move in the direction of the arrow Z in FIG. 4) the measuring table 24. Therefore, the entire internal surface of the hole 28, as shown in FIG. 13, is sequentially scanned by the laser beam 21 from the lower end to the upper end of the hole 28. The reflected laser beam 21a of the laser beam 21, as shown in FIG. 4, is introduced into the half-silvered mirror 23, photosensor 34, amplifier 35, analog signal processing circuit 36, A/D converter 37, and interface 38. As a result, the printer 40 and floppy disc 41 sequentially store therein the condition of the entire internal surface of the hole 28 from the lower end to the upper end of the hole 28. Simultaneously, the CRT image display means 42 displays an image of the entire internal surface of the hole 28 sequentially from the lower to the upper end of the hole 28. Therefore, from the image displayed by the CRT image display means 42 and the contents recorded in the printer, the condition of the entire internal surface of the hole 28 can be known.

The scan by the laser beam 21 finishes in such a manner that since the reflected laser beam 21a of laser beam 21 is not reflected by the internal surface of the hole 28 and not impringed to the photosensor 34 when the reflecting surface 27 of wire rod 26 projects outwardly from the upper end of the hole 28, the computer 39 puts out a drive end signal on the basis of variation in quantity of received beam at the photosensor 34. Such downward (in the Z direction) movement of the measuring table 24 is detected by the first position detection circuit 45 connected to the measuring table driving mechanism 44, the detected value being given into the computer 39. A thickness of the multilayer printed board 25 is previously introduced into the computer 39 so that, when the measuring table 24 moves downwardly (in the Z direction) in an excessive amount larger than the thickness of board 25, the computer 39 is adapted to put out a stop signal, thereby avoiding such excessive movement. Similarly, when an amount of lateral (in the X direction) movement of the measuring table 24 is about to exceed a diameter of the bore 24a of measuring table 24 during the measurement of the diameter of the hole 28 of the multilayer printed board 25, the computer 39 puts out a stop signal to stop movement of the measuring table 24. Thus, the smaller diameter wire rod 26 is prevented from breakdown caused by the excessive movement of measuring table 24.

In the aforesaid embodiment, the smaller diameter wire rod 26 rotates and the measuring table 24 moves upwardly for observing the internal surface of the hole 28, but alternatively, the measuring table 24 may be rotated and simultaneously the smaller diameter wire rod 26 may be vertically moved.

What is claimed:

1. In a method of observing the condition of the internal surface of a small hole formed in an inspected object and to be measured, wherein a smaller diameter wire rod smaller in diameter than said small hole and forming a reflecting surface at the utmost end is inserted at the utmost end portion into said small hole coaxially therewith, a laser beam is impinged onto said reflection surface at the utmost end through a half-silvered mirror while rotating said smaller diameter wire rod relatively to the internal surface of said small hole, so that said laser beam is reflected by said reflecting surface and impinged onto the internal surface of said small hole, the laser beam reflected from the internal surface of said small hole is reflected by said reflecting surface and reaches said half-silvered mirror so as to be reflected therefrom, and the reflected laser beam reflected from said half silvered mirror is guided to image processing means, the improvement of aligning said hole with said smaller diameter wire rod prior to carrying out the steps recited hereinabove characterized in that said reflecting surface at the utmost end of said smaller diameter wire rod is disposed outside of said inspected object to thereby prepare a condition capable of detecting the laser beam, which is passed through said small hole, incident on said reflecting surface and thereafter reflected by said reflecting surface, said inspected object is moved relatively to said smaller diameter wire rod in a first direction which is perpendicular to the axis of said small hole to detect that the laser beam is shaded by both side edges of said small hole in said first direction, thereby obtaining an amount of a first movement of said inspected object at that time, said smaller diameter wire rod is positioned corresponding to a half value of said amount of movement of said inspected object, said inspected object is moved relatively to said smaller diameter wire rod in a second direction perpendicular to both the axial direction of said small hole and said first direction of said inspected object, while maintaining the positioning condition of said smaller diameter wire rod in said first direction, thereby detecting that the laser beam is shaded by both side edges of said small hole in said second direction of said inspected body and obtaining an amount of a second movement at that time, and said smaller diameter wire rod is positioned corresponding to a half value of an amount of said second movement.

2. In a method of observing the condition of the internal surface of a small hole formed in an inspected object and to be measured, characterized in that a smaller diameter wire rod smaller in diameter than said small hole and forming a reflecting surface at the utmost end is inserted at the utmost end portion into said small hole coaxially therewith, a laser beam is impinged onto said reflecting surface at the utmost end through a half-silvered mirror while rotating said smaller diameter wire rod relatively to the internal surface of said small hole, so that said laser beam is reflected by said reflecting surface and impinged onto the internal surface of said small hole, the laser beam reflected from the internal surface of said small hole is reflected by said reflecting surface and reaches said half-silvered mirror so as to be reflected therefrom, the reflected laser beam reflected from said half silvered mirror is guided to image processing means, and said smaller diameter wire rod is axially moved relative to said small hole, thereby observing the condition of the entire internal surface of said small hole, wherein when said reflecting surface of said smaller diameter wire rod projects outside said inspected object beyond one axial end of said small hole, the laser beam is not reflected by the internal surface of said small hole to produce quantity of incident laser beam on said image processing means, thereby detecting that said reflecting surface projects beyond said end.

* * * * *